US012741080B2

(12) United States Patent
Almond

(10) Patent No.: US 12,741,080 B2
(45) Date of Patent: Sep. 22, 2026

(54) ADAPTABLE PORTABLE DOUCHE APPARATUS

(71) Applicant: Mr Bear Enterprise, LLC, Falls Church, VA (US)

(72) Inventor: Glen P Almond, Falls Church, VA (US)

( * ) Notice: Subject to any disclaimer, the term of this patent is extended or adjusted under 35 U.S.C. 154(b) by 160 days.

(21) Appl. No.: 18/231,687

(22) Filed: Aug. 8, 2023

(65) Prior Publication Data

US 2025/0050010 A1 Feb. 13, 2025

(51) Int. Cl.
*A61M 3/02* (2006.01)
*A61M 3/06* (2006.01)

(52) U.S. Cl.
CPC ............ *A61M 3/0279* (2013.01); *A61M 3/06* (2013.01)

(58) Field of Classification Search
CPC ........ A61M 3/02; A61M 3/0279; A61M 3/06; F16L 255/14; F16L 3/1041
USPC .......................................................... 604/257
See application file for complete search history.

(56) References Cited

U.S. PATENT DOCUMENTS 2,588,381 A * 3/1952 Gow .................. A61M 3/0262 604/215
4,519,794 A 5/1985 Sneider
D750,771 S 3/2016 Malin et al.
D896,368 S 9/2020 Zhang
D948,708 S 4/2022 Zhang
D948,709 S 4/2022 Zhang
D1,006,985 S 12/2023 Zeka
11,918,509 B1 3/2024 Macdonald et al.
D1,105,415 S 12/2025 Peng (Continued)

FOREIGN PATENT DOCUMENTS

CN 3257658D 10/2002
CN 2638739 Y 9/2004
CN 303952098 S 11/2016
KR 3003138390000 12/2002

OTHER PUBLICATIONS

PCT Preliminary Report on Patentability, Issued Feb. 6, 2026, in PCT/US2024/20841, Authorized Officer Simin Baharlou (file name PCTUS2024020841-ipp1-000034-en-XX-20260210.pdf). Note that while this document issued Feb. 6, 2026, it is a conversion of the PCT International Search Report and Written Opinion disclosed in the IDS filed in the present application on Jan. 11, 2026.

(Continued)

*Primary Examiner* — Philip E Stimpert
(74) *Attorney, Agent, or Firm* — Robert L Protheroe

(57) ABSTRACT

A douche apparatus adaptable to a bottle and configurable for storage and portability may comprise a nozzle and an adapter assembly having one or more bottle adapters, a nozzle attachment end, a bottle attachment end and an adapter assembly central portion. The douche apparatus is adaptable to a bottle having bottle threads mateable to the bottle attachment end, and is configurable for storage and portability, wherein the nozzle may be detached from the adapter assembly and be situated within the adapter assembly central portion. The douche apparatus may further comprise a case having a case housing and a case cap having an interior side comprising threads mateable to the bottle attachment end, wherein the adapter assembly may be attached to the interior side of the case cap prior to an attachment of the case cap to the case housing.

11 Claims, 8 Drawing Sheets

(56) References Cited

U.S. PATENT DOCUMENTS

| | | | | |
|---|---|---|---|---|
| 2003/0212382 | A1 | 11/2003 | Abbott et al. | |
| 2009/0208271 | A1* | 8/2009 | Krohn | F16L 41/021 403/4 |
| 2010/0211021 | A1* | 8/2010 | Wong | A61M 3/0279 604/247 |
| 2017/0340805 | A1* | 11/2017 | Novinger | A61M 3/0279 |
| 2020/0121136 | A1 | 4/2020 | DeBlasi | |
| 2020/0390961 | A1 | 12/2020 | Zhang et al. | |
| 2022/0143300 | A1 | 5/2022 | Calvin et al. | |
| 2023/0032289 | A1 | 2/2023 | Hughes et al. | |
| 2025/0375566 | A1 | 12/2025 | Kerwell et al. | |

OTHER PUBLICATIONS

Restriction Requirement in U.S. Appl. No. 29/965,277, Mailed Jan. 26, 2026, (file name 29965277—Restriction—Jan. 26, 2026).

PCT International Search Report and Written Opinion, Mailed Jul. 25, 2024, in PCT/US 24/20841, Authorized Officer Kari Rodriquez.

Office Action Ex Parte Quayle Action in 29965277, May 15, 2026, File—N01-29965277_05-15-2026_CTEQ.pdf.

Office Action Non-Final in 18401546, May 19, 2026, File—N02-18401546_05-19-2026_CTNF.pdf.

Ribbed Anal Douche, Calexotics, [Post date unknown], [Site seen: Apr. 14, 2026], URL: https://strokedego.ca/products/ribbed-anal-douche (Year: 2026); Cited with Ex Parte Quayle Action in 29965277, May 15, 2026 File: N03-Ribbed_NPL.pdf.

Calexotics ribbed anal douche, Calexotics, [Post date unknown], [Site seen: Apr. 14, 2026], URL: https://www.walmart.com/ip/CalExotics-Ribbed-Anal-Douche-2-Unique-Attachmments-Cleaning-System/138686496 (Year: 2026); Cited with Ex Parte Quayle Action in 29965277, May 15, 2026 File: N04-Calexotics_NPL.pdf.

TDA-A, Me. Bear, whatistda/tda-a [Post date unknown], [Site seen: Apr. 14, 2026], URL: https://whatistda.com/tda-a (Year: 2026); Cited with Ex Parte Quayle Action in 29965277, May 15, 2026 File: N05-TDA-A_NPL.pdf.

* cited by examiner

ADAPTABLE PORTABLE DOUCHE APPARATUS

CROSS-REFERENCE TO RELATED APPLICATIONS

Not Applicable

BACKGROUND

The present disclosure relates to douche apparatuses and more particularly relates to an adaptable portable douche apparatus.

SUMMARY

Various implementations of a douche apparatus of the present invention are disclosed. In some aspects, the techniques described herein relate to a douche apparatus adaptable to a bottle and configurable for storage and portability, including: a nozzle having a nozzle channel through which a liquid may flow during use, a proximate end having a nozzle attachment feature, a distal end having a nozzle tip and a nozzle body extending from the nozzle attachment feature up to and including the nozzle tip including a nozzle wall circumscribing the nozzle channel, wherein the nozzle has at least one orifice disposed on the nozzle tip or the nozzle wall through which a liquid may be dispensed during use; and an adapter assembly having one or more adapters, a nozzle attachment end mateable to the nozzle attachment feature removably attaching the nozzle to the adapter assembly, a bottle attachment end including bottle attachment threads, and an adapter assembly central portion through which a liquid may flow during use, wherein: the douche apparatus is configurable for storage and portability, wherein the nozzle may be detached from the adapter assembly and the nozzle body may be situated at least partially within the adapter assembly central portion; and the douche apparatus is adaptable to a squeezable bottle for use, wherein the squeezable bottle includes a volume of liquid and has bottle threads, wherein the bottle attachment threads are mateable to the bottle threads.

In some aspects, the techniques described herein relate to a douche apparatus, wherein the adapter assembly has a single adapter, and the single adapter includes the nozzle attachment end and the bottle attachment end.

In some aspects, the techniques described herein relate to a douche apparatus, wherein the bottle attachment end is a second bottle attachment end, and the adapter assembly includes: a first adapter including the nozzle attachment end and a first bottle attachment end; and a second adapter including the second bottle attachment end and an adapter attachment end mateable and removably attached to the first bottle attachment end, wherein: the bottle attachment threads are second bottle attachment threads; the first bottle attachment end includes first bottle attachment threads mateable with threads of a bottle including bottle threads of a first type; the second bottle attachment end includes the second bottle attachment threads mateable with threads of a bottle including bottle threads of a second type; the douche apparatus is adaptable to a squeezable bottle for use, wherein the squeezable bottle includes a volume of liquid and has bottle threads of the second type; and the douche apparatus is adaptable to a squeezable bottle for use, wherein the squeezable bottle includes a volume of liquid and has bottle threads of the first type, and the second adapter is detached from the adapter assembly thereby exposing the first bottle attachment end including the first bottle attachment threads.

In some aspects, the techniques described herein relate to a douche apparatus, wherein the bottle attachment end is a third bottle attachment end, and the adapter assembly includes: a first adapter including the nozzle attachment end and a first bottle attachment end; a second adapter including a second bottle attachment end and a first adapter attachment end mateable and removably attached to the first bottle attachment end; and a third adapter including the third bottle attachment end and a second adapter attachment end mateable and removably attached to the second bottle attachment end, wherein: the bottle attachment threads are third bottle attachment threads; the first bottle attachment end includes first bottle attachment threads mateable with threads of a bottle including bottle threads of a first type; the second bottle attachment end includes second bottle attachment threads mateable with threads of a bottle including bottle threads of a second type; the third bottle attachment end includes the third bottle attachment threads mateable with threads of a bottle including bottle threads of a third type; the douche apparatus is adaptable to a squeezable bottle for use, wherein the squeezable bottle includes a volume of liquid and has bottle threads of a third type; the douche apparatus is adaptable to a squeezable bottle for use, wherein the squeezable bottle includes a volume of liquid and has bottle threads of a second type, and the third adapter is detached from the adapter assembly thereby exposing the second bottle attachment end including the second bottle attachment threads; and the douche apparatus is adaptable to a squeezable bottle for use, wherein the squeezable bottle includes a volume of liquid and has bottle threads of the first type, and the second adapter and third adapter are detached from the adapter assembly thereby exposing the first bottle attachment end including the first bottle attachment threads.

In some aspects, the techniques described herein relate to a douche apparatus, wherein when configured for storage and portability, the nozzle body may be situated wholly within the adapter assembly central portion.

In some aspects, the techniques described herein relate to a douche apparatus, wherein when configured for storage and portability, the nozzle tip is directed towards the bottle attachment end and the nozzle attachment feature is removably attached to the nozzle attachment end.

In some aspects, the techniques described herein relate to a douche apparatus, further including a case having a case housing and a case cap, wherein: the case cap is removably attachable to the case housing; the case cap has an exterior side and an interior side, wherein, when attached to the case housing, the interior side is directed towards an interior of the case housing; and the case cap includes threads mateable to the bottle attachment end, wherein the adapter assembly is configured to be removably attached to the interior side of the case cap prior to an attachment of the case cap to the case housing, thereby storing the adapter assembly within the case.

In some aspects, the techniques described herein relate to a douche apparatus, wherein the case cap further includes threads mateable to the nozzle attachment feature, wherein the nozzle is configured to be removably attached to the interior side of the case cap and be situated at least in part within the adapter assembly central portion.

In some aspects, the techniques described herein relate to a douche apparatus, wherein the exterior side of the case cap includes a recess area proximate to a graspable member of the case cap.

In some aspects, the techniques described herein relate to a douche apparatus, further including a stimulation device removably attachable to the nozzle attachment end of the adapter assembly.

In some aspects, the techniques described herein relate to a douche apparatus, wherein the stimulation device includes a vibrator mechanism and a power source for the vibrator mechanism.

In some aspects, the techniques described herein relate to a douche apparatus, further including a check valve, wherein the check valve is configured to allow liquid to flow through the nozzle channel and dispense through the at least one orifice and prevent liquid from flowing in a reverse direction thereof.

In some aspects, the techniques described herein relate to a douche apparatus, wherein each of the one or more adapters include a plurality of nubs configured to facilitate a grip thereon.

In some aspects, the techniques described herein relate to a douche apparatus adaptable to a bottle and configurable for storage and portability, including: a nozzle having a nozzle channel through which a liquid may flow during use, a proximate end having a nozzle attachment feature, a distal end having a nozzle tip and a nozzle body extending from the nozzle attachment feature up to and including the nozzle tip including a nozzle wall circumscribing the nozzle channel, wherein the nozzle has at least one orifice disposed on the nozzle tip or the nozzle wall through which a liquid may be dispensed during use; one or more adapters, each including a nozzle attachment end mateable to the nozzle attachment feature removably attaching the nozzle to one of the one or more adapters, a bottle attachment end including bottle attachment threads, and an adapter central portion through which a liquid may flow during use; and a case having a case housing and a case cap, wherein: the case cap is removably attachable to the case housing; the case cap has an exterior side and an interior side, wherein, when attached to the case housing, the interior side is directed towards an interior of the case housing; the case cap includes threads mateable to the nozzle attachment feature, wherein each of the one or more adapters may be stacked on the case cap having the nozzle body situated at least in part within at least one adapter central portion; and the douche apparatus is adaptable to a squeezable bottle for use, wherein the squeezable bottle includes a volume of liquid and has bottle threads, wherein the bottle attachment threads of one of the one or more adapters are mateable to the bottle threads.

In some aspects, the techniques described herein relate to a douche apparatus, wherein the douche apparatus has a single adapter, and the single adapter includes bottle attachment threads of a first type.

In some aspects, the techniques described herein relate to a douche apparatus, wherein the douche apparatus includes a first adapter and a second adapter, wherein the first adapter includes bottle attachment threads of a first type and the second adapter includes bottle attachment threads of a second type.

In some aspects, the techniques described herein relate to a douche apparatus, wherein the douche apparatus includes a first adapter, a second adapter and a third adapter, wherein the first adapter includes bottle attachment threads of a first type, the second adapter includes bottle attachment threads of a second type and the third adapter includes bottle attachment threads of a third type.

In some aspects, the techniques described herein relate to a douche apparatus, wherein when configured for storage and portability, the nozzle body may be situated wholly within the combined central portions of the first adapter, second adapter and third adapter.

In some aspects, the techniques described herein relate to a douche apparatus, wherein the exterior side of the case cap includes a recess area proximate to a graspable member of the case cap.

In some aspects, the techniques described herein relate to a douche apparatus, further including a check valve, wherein the check valve is configured to allow liquid to flow through the nozzle channel and dispense through the at least one orifice and prevent liquid from flowing in a reverse direction thereof.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of the disclosed subject matter.

FIG. 7A depicts a side elevation view of a first bottle adapter of the douche apparatus of FIG. 6A.

FIG. 7B depicts a cross-section of the bottle adapter of FIG. 7A.

FIG. 7C depicts a side elevation view of a second bottle adapter of the douche apparatus of FIG. 6A.

FIG. 7D depicts a cross-section of the bottle adapter of FIG. 7C.

FIG. 7E depicts a side elevation view of a third bottle adapter of the douche apparatus of FIG. 6A.

FIG. 7F depicts a cross-section of the bottle adapter of FIG. 7E.

DETAILED DESCRIPTION

Detailed implementations of a douche apparatus of the present invention are disclosed herein. It will be apparent to those skilled in the art that while the disclosed implementations are instructive in how to practice the invention presently disclosed herein, they are not exhaustive and other implementations which are within the scope of the appended claims may be conceived when given the benefit of the present disclosure. As such, the implementations of the present disclosure may be considered instructive but not restrictive.

The following detailed implementations refer to the accompanying drawings. The same reference number may appear in multiple figures of the drawings and when appearing in multiple figures will identify the same or similar elements.

Figures 1A, 1B, 1C, 1D, 1E:
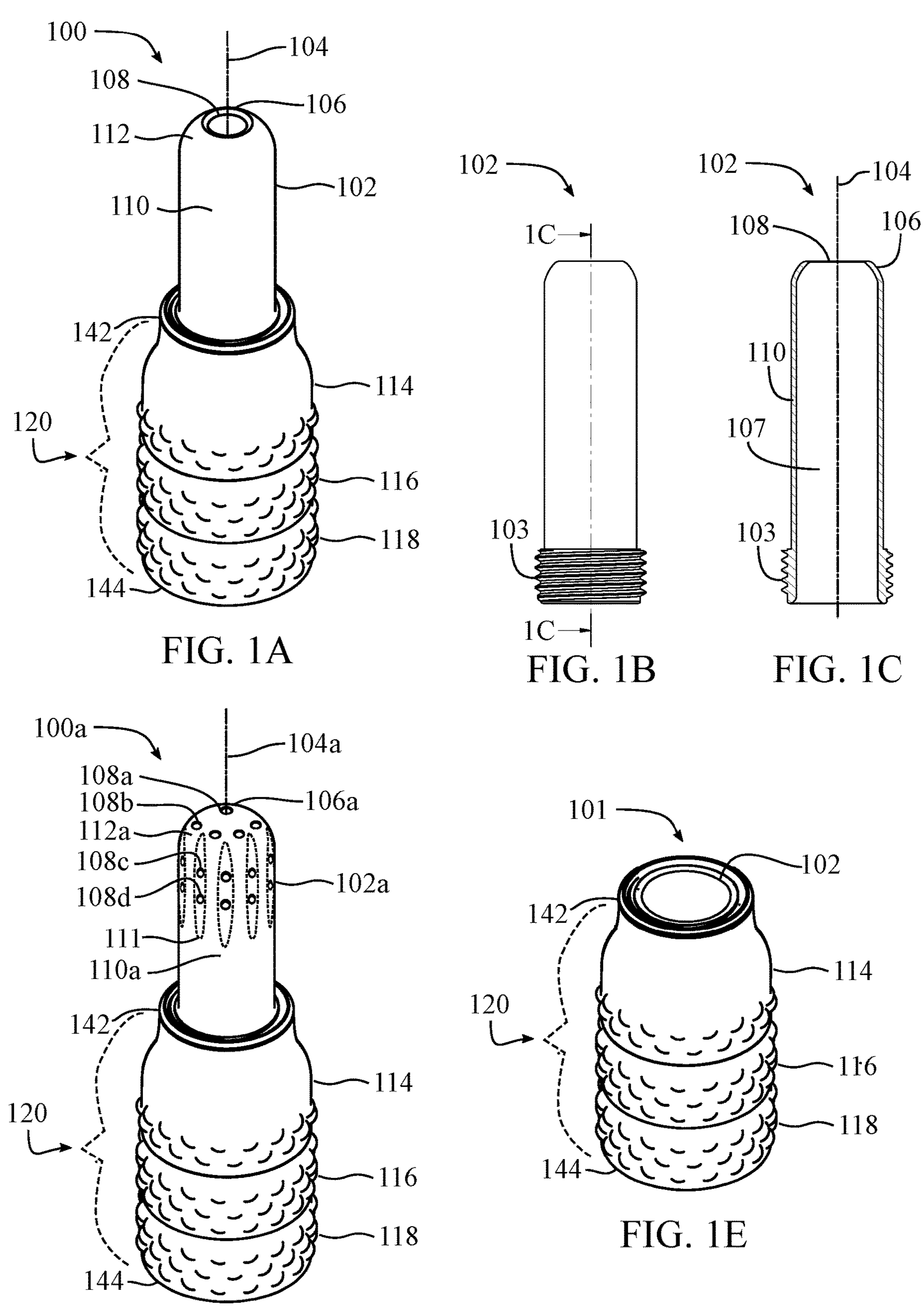
FIG. 1A depicts a perspective view of an example implementation of a douche apparatus of the present invention.
FIG. 1B depicts an example implementation of a nozzle detached from the douche apparatus of FIG. 1A and shown in a side elevation view cross-section.
FIG. 1C a cross-section of the example implementation of the nozzle of FIG. 1B.
FIG. 1D depicts a perspective view of an example implementation of a douche apparatus of the present invention having a nozzle, wherein the nozzle comprises a plurality of orifices.
FIG. 1E depicts a perspective view of the douche apparatus of FIG. 1A (or FIG. 1D) configured in a storage-orientation.

FIG. 1A depicts a perspective view of an example implementation of a douche apparatus 100 of the present invention. Douche apparatus 100 comprises a nozzle 102 configured to be insertable into a cavity to be douched and to dispense a douche liquid therein. Nozzle 102 may be elongate and terminate at its distal end in a rounded nozzle tip 106 wherein nozzle tip 106 has an orifice 108 through which a liquid may be dispensed. FIG. 1B and FIG. 1C depict an example implementation of nozzle 102 detached from douche apparatus 100 and shown in a side elevation view and a cross-section view thereof, respectively. At its proximate end, nozzle 102 may comprise a nozzle attachment feature 103, which in some implementations may be male threads as shown in FIG. 1B. As will be apparent to those skilled in the art, in some implementations a mating feature other than threads as depicted in FIG. 1B are possible and within the scope of the appended claims, such as a bayonet mount or other such suitable mateable feature. In some implementations, nozzle attachment feature 103 may comprise a ½ inch male NPS thread, where NPS refers to National Pipe Straight of the American National Standard Pipe Thread standards; in some implementations nozzle attachment feature 103 may comprise a ½ inch male BSP parallel thread, where BSP refers to British Standard Pipe standards, or may comprise another suitable thread. FIG. 1B shows section line 1C-1C, and FIG. 1C depicts the indicated cross-section view, wherein an axis 104 may be circumscribed by a nozzle wall 110 forming a nozzle channel 107 having an opening at nozzle attachment feature 103 into which liquid may flow and an orifice 108 from which liquid may flow and be dispensed. A nozzle body may be a portion of nozzle 102 extending from nozzle attachment feature 103 up to and including nozzle tip 106.

An elongate shape of nozzle 102 and rounded configuration of nozzle tip 106 may facilitate penetration into a cavity and reduce or eliminate discomfort associated with such penetration. A user of douche apparatus 100 may apply a lubricant to tip 106 to further facilitate penetration into a cavity. Nozzle 102 may comprise one or more orifices or openings though which liquid may flow and be dispensed, such as a single orifice such as orifice 108 as depicted in FIG. 1A which may be configured to dispense liquid at nozzle tip 106. Configured as shown in FIG. 1A, nozzle 102 can penetrate a cavity, such as a vaginal or anal cavity, and dispense a liquid though orifice 108 within the penetrated cavity thereby douching the penetrated cavity. In the example implementation of FIG. 1A, a douche liquid dispensed with a force sufficient to project the liquid from nozzle 102 through orifice 108 will tend to direct the liquid along axis 104 of nozzle 102, however many other nozzle and orifice configurations are possible. For example, in some implementations, one or a plurality of orifices may be disposed on wall 110 of nozzle 102 and/or a sloping wall 112 of nozzle tip 106 such that a jet or spray of dispensed liquid can issue from orifices disposed off-axis (not shown in FIG. 1A) and project off-angle from axis 104 of nozzle 102, thereby providing alternative spray patterns to that of a spray pattern primarily directed along axis 104. Users may prefer a spray pattern directed solely generally along axis 104 as may be produced by nozzle 102 of the example implementation of FIG. 1A, or they may prefer a nozzle configured to produce a spray pattern which alternatively or additionally provides an off-angle spray pattern from axis 104 of nozzle 102.

Douche apparatus 100 may comprise an adapter assembly 120 having one or more bottle adapters, wherein three are depicted in the example implementation of FIG. 1A, namely bottle adapter 114, to which nozzle 102 is attached, bottle adapter 116 and bottle adapter 118. Nozzle 102 may have a nozzle attachment feature at its proximate end (not visible in FIG. 1A) configured to mate with a nozzle attachment end 142 of adapter assembly 120 (comprised by bottle adapter 114 of adapter assembly 120) which is at the opposite end from a bottle attachment end 144 of adapter assembly 120. Each bottle adapter, i.e., bottle adapter 114, bottle adapter 116 and bottle adapter 118, may be configured to attach at least a portion of douche apparatus 100 comprising nozzle 102 to a flexible sided container (e.g., a squeezable bottle) comprising a volume of liquid, such as for example, a conventional plastic water bottle comprising water. When using water, such as that found in a conventional plastic water bottle, a user may choose to add salt to produce a saline solution or choose to add some other desired additive prior to douching.

FIG. 1D depicts a perspective view of an example implementation of a douche apparatus 100*a* of the present invention having a nozzle 102*a*, wherein nozzle 102*a* comprises a tip 106*a*, a wall 110*a* and a plurality of orifices, such as orifice 108*a*, orifice 108*b* and orifice 108*c*. In the example implementation of FIG. 1D, orifice 108*a* is located on tip 106*a* along axis 104*a*, orifice 108*b* is located on sloping wall 112*a* of tip 106*a* and orifice 108*c* is located on wall 110*a* of nozzle 102*a*, wherein a douche liquid dispensed with a force sufficient to project the liquid from nozzle 102*a* through orifices orifice 108*a*, orifice 108*b* and orifice 108*c* will tend to direct liquid through orifice 108*a* along axis 104*a* and direct liquid though orifice 108*b* and orifice 108*c* off-angle from axis 104*a*. A spray pattern produced by the orifice configuration depicted in FIG. 1D may facilitate cleansing and/or medicating of sidewalls of a cavity being douched through off-angle spray which may thereby direct liquid spray toward cavity sidewalls. In some implementations, only off-axis orifices, e.g., such as orifice 108*b* and orifice 108*c* may be configured, i.e. where orifice 108*a* is not configured. As will be apparent to those skilled in the art, many possible orifice configurations are possible.

An orifice located on a nozzle wall may be blocked by intimate contact between a cavity wall and nozzle wall 110*a*, wherein the cavity wall acts to block the orifice thereby impeding flow therethrough. In the example implementation of FIG. 1D, nozzle 102*a* comprises recessed portions in wall 110*a*, such as recessed portion 111. Recessed portion 111 may comprise orifices 108*c* and 108*b*, wherein orifice 108*c* and orifice 108*d* may remain unimpeded despite intimate contact between a cavity wall by virtue of their recess providing a gap between them and the cavity wall.

Douche apparatus 100*a* may comprise an adapter assembly 120 having one or more bottle adapters, wherein three are depicted in the example implementation of FIG. 1D, namely bottle adapter 114, to which nozzle 102*a* is attached, bottle adapter 116 and bottle adapter 118. Nozzle 102*a* may have a nozzle attachment feature at its proximate end (not visible in FIG. 1D) configured to mate with a nozzle attachment end 142 of adapter assembly 120 (comprised by bottle adapter 114 of adapter assembly 120) which is at the opposite end from a bottle attachment end 144 of adapter assembly 120. Each bottle adapter, i.e., bottle adapter 114, bottle adapter 116 and bottle adapter 118, may be configured to attach at least a portion of douche apparatus 100*a* comprising nozzle 102*a* to a flexible sided container (e.g., a squeezable bottle) comprising a volume of liquid, such as for example, a conventional plastic water bottle comprising water. When using water, such as that found in a conventional plastic water bottle, a user may choose to add salt to produce a saline solution or choose to add some other desired additive prior to douching.

FIG. 1E depicts a perspective view of the douche apparatus 100 (or 100*a*) of FIG. 1A (or FIG. 1D) configured in a storage-orientation, wherein nozzle 102 (or nozzle 102*a*) may be inserted nozzle tip 106 (or 106*a*) end (i.e., distal end of nozzle 102 or 102*a*) first into a central portion of adapter assembly 120, also referred to as "adapter assembly central portion", comprising bottle adapter 114, bottle adapter 116 and bottle adapter 118, thereby reducing the overall length of the storage-configuration depicted in FIG. 1E from that of a use-configuration depicted in FIG. 1A (or FIG. 1D), thereby enhancing its portability and the ability to carry douche apparatus 101, as shown in FIG. 1E or in a case (not shown in FIG. 1E), in a pants pocket, a shirt pocket, a back pack, a carrying bag or the like. A nozzle attachment feature of nozzle 102 (or 102*a*) (not visible in FIG. 1E) may be configured to mate with a mateable feature of bottle adapter 114 (not visible in FIG. 1E) at a nozzle attachment end 142 of adapter assembly 120 which is at the opposite end from a bottle attachment end 144 of adapter assembly 120.

Figures 2A, 2B, 2C:
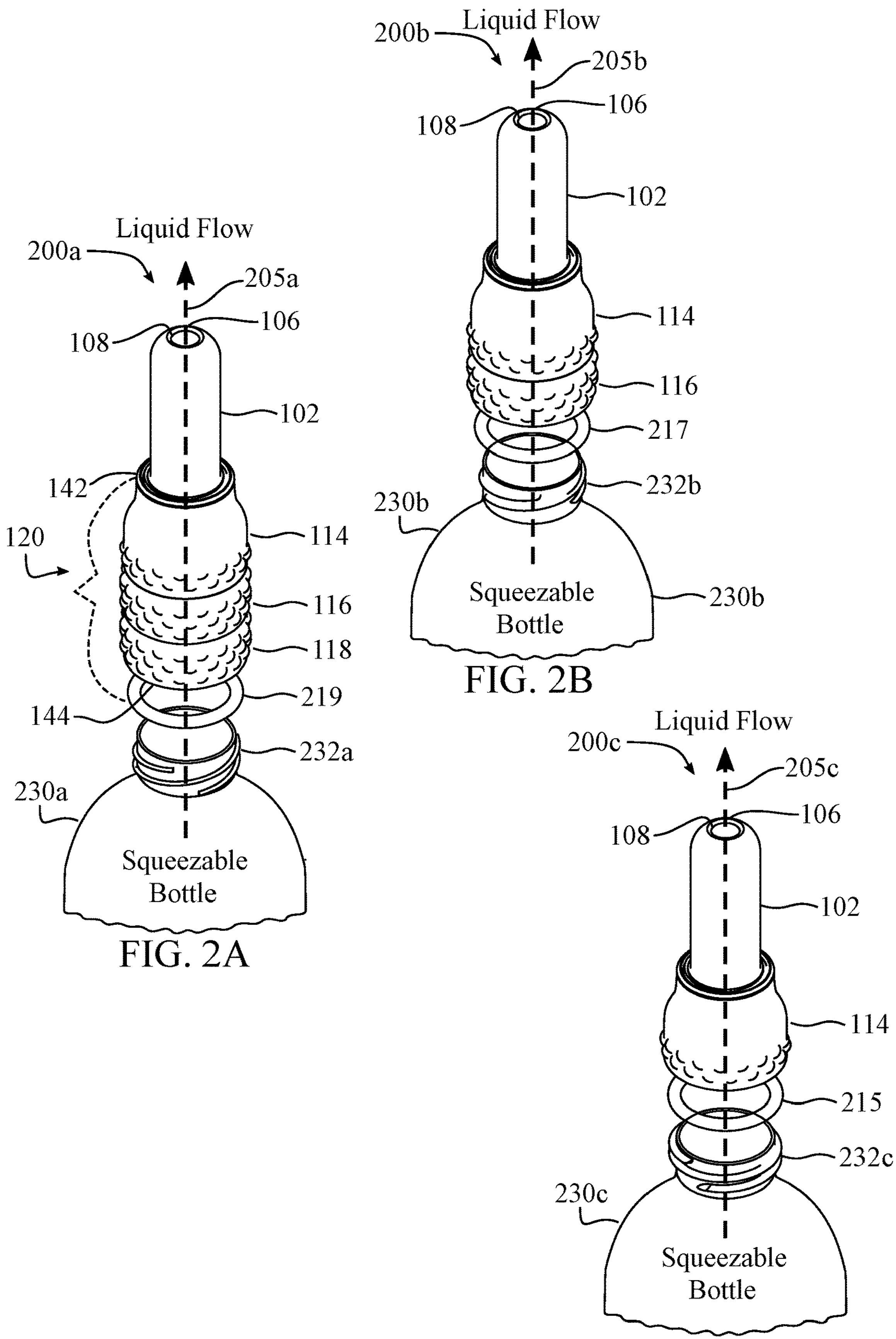
FIG. 2A depicts a partially exploded perspective view of the douche apparatus of FIG. 1A adapted to a squeezable bottle having bottle threads of a third type.
FIG. 2B depicts a partially exploded perspective view of the douche apparatus of FIG. 1A adapted to a squeezable bottle having bottle threads of a second type.
FIG. 2C depicts a partially exploded perspective view of the douche apparatus of FIG. 1A adapted to a squeezable bottle having bottle threads of a first type.

FIG. 2A, FIG. 2B and FIG. 2C depict partially exploded perspective views of douche apparatus 200*a*, douche apparatus 200*b* and douche apparatus 200*c* adapted to partially depicted squeezable bottles, i.e., squeezable bottle 230*a*, squeezable bottle 230*b* and squeezable bottle 230*c*, respectively, wherein a path and direction of liquid flow from squeezable bottle 230*a*, squeezable bottle 230*b* and squeezable bottle 230*c* through central portions of each bottle adapter and nozzle channels of douche apparatus 200*a*, douche apparatus 200*b* and douche apparatus 200*c* are indicated by arrow 205*a*, arrow 205*b* and arrow 205*c*, respectively. Douche apparatus 200*a* (which may correspond to douche apparatus 100 of FIG. 1A) comprising adapter assembly 120 and nozzle 102 which may be attached at its nozzle attachment end 142 and bottle attachment end 144 may be attached to bottle threads 232*a* of squeezable bottle 230*a* by mating bottle attachment threads (not visible in FIG. 2A) of bottle adapter 118, wherein an O-ring 219 may be seated in bottle adapter 118 and provide a liquid seal between apparatus 200*a* and squeezable bottle 230*a*. In some implementations, a rubber washer, gasket or other sealing member may be used instead of O-ring 219. Douche apparatus 200*b* (which may correspond to douche apparatus 100 of FIG. 1A having bottle adapter 118 and O-ring 219 removed) may be attached to male threads 232*b* of squeezable bottle 230*b* by mating female threads (not visible in FIG. 2B) of bottle adapter 116, wherein an O-ring 217 may be seated in bottle adapter 116 and provide a liquid seal between apparatus 200*b* and squeezable bottle 230*b*. In some implementations, a rubber washer, gasket or other sealing member may be used instead of O-ring 217. Douche apparatus 200*c* (which may correspond to douche apparatus 100 of FIG. 1A having bottle adapter 118, O-ring 219, bottle adapter 116 and O-ring 217 removed) may be attached to male threads 232*c* of squeezable bottle 230*c* by mating female threads (not visible in FIG. 2C) of bottle adapter 114, wherein an O-ring 215 may be seated in bottle adapter 114 and provide a liquid seal between apparatus 200*c* and squeezable bottle 230*c*. In some implementations, a rubber washer, gasket or other sealing member may be used instead of O-ring 215. In the example implementation of FIG. 2A, douche apparatus 200*a* may be douche apparatus 100 of FIG. 1A, wherein bottle adapter 118 comprises a first bottle attachment end configured to mate with bottle 230*a* having male threads 232*a* of a third type, bottle adapter 116 is configured to mate with squeezable bottle 230*b* (where bottle adapter 118 is detached from apparatus 100 exposing a second bottle attachment end as shown in FIG. 2B) having male threads 232*b* of a second type, and bottle adapter 114 is configured to mate with squeezable bottle 230*c* (where bottle adapter 118 and bottle adapter 116 are detached from apparatus 100 as shown in FIG. 2C exposing a third bottle attachment end) having male threads 232*c* of a first type, thereby enabling douche apparatus 100 of FIG. 1A to be adaptable to any bottle having a thread type of the third type (e.g. squeezable bottle 230*a* having threads 232*a*), second type (e.g. squeezable bottle 230*b* having threads 232*b*), or first type (e.g. squeezable bottle 230*c* having threads 232*c*). In some implementations, bottle threads of a third type may be compatible with a 1-liter Dasani brand water bottle. In some implementations, bottle threads of a second type may be compatible with a Poland Springs brand 1.5-liter water bottle, a Royal Farms Mountain Spring brand 1-liter water bottle and a Deer Park brand 1.5-liter water bottle. In some implementations, bottle threads of a first type may be compatible with a 0.5-liter Wellsley Farms brand water bottle. As will be apparent to those skilled in the art, in some implementations bottle adapter 114, bottle adapter 116 and bottle adapter 118 may be configured to be compatible with other types of bottle threads as those comprised by the aforementioned brands of water bottles, and such implementations are within the scope of the appended claims.

Figures 3A, 3B, 3C, 3D, 3E, 3F, 3G:
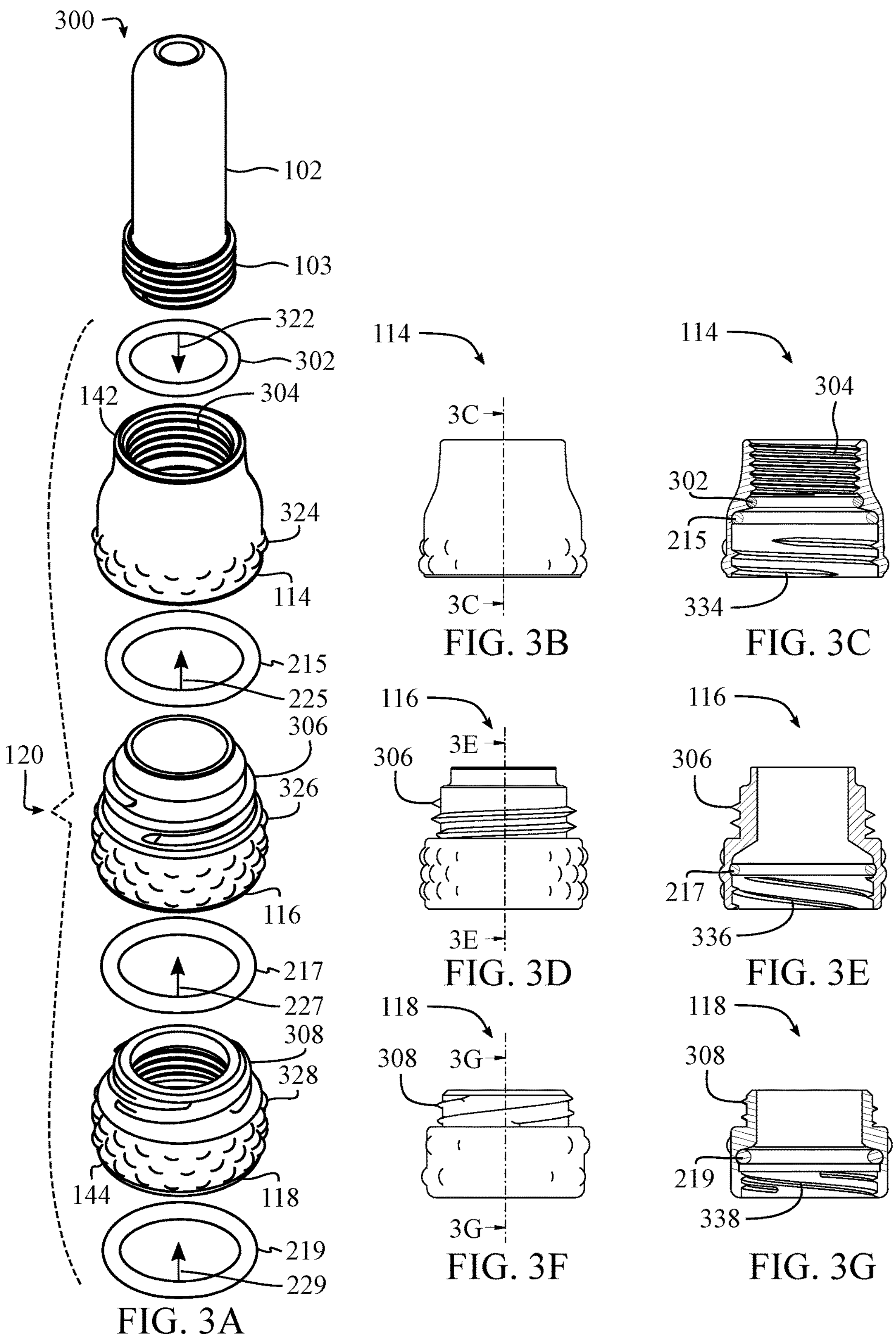
FIG. 3A depicts a perspective view of an exploded assembly of the douche apparatus of FIG. 1A.
FIG. 3B depicts a side elevation view of an example first bottle adapter of the douche apparatus of FIG. 3A.
FIG. 3C depicts a cross-section of the bottle adapter of FIG. 3B.
FIG. 3D depicts a side elevation view of an example second bottle adapter of the douche apparatus of FIG. 3A.
FIG. 3E depicts a cross-section of the bottle adapter of FIG. 3D.
FIG. 3F depicts a side elevation view of an example third bottle adapter of the douche apparatus of FIG. 3A.
FIG. 3G depicts a cross-section of the bottle adapter of FIG. 3F.

FIG. 3A, depicts a perspective view of an example exploded assembly 300 of a douche apparatus, such as douche apparatus 100 of FIG. 1A comprising a nozzle 102 having a nozzle attachment feature 103 at its proximal end which is configured to be mateable and removably attachable to adapter assembly 120 (shown in exploded view). Adapter assembly 120 may comprise one or more bottle adapters, such as bottle adapter 114, bottle adapter 116 and bottle adapter 118 as is shown in the example implementation depicted in FIG. 3A. Adapter assembly 120 may further comprise O-ring 302, O-ring 215, O-ring 217 and O-ring 219 which are not visible in views of adapter assembly 120 depicted in FIG. 1A, FIG. 1D, FIG. 1E and FIG. 2A. O-ring 302, O-ring 215, O-ring 217 and O-ring 219 are shown in relation to bottle adapter 114, bottle adapter 116 and bottle adapter 118, wherein each O-ring is depicted with an arrow directed to a bottle adapter in which they may first be seated prior to an assembly of adapter assembly 120 and an attachment of nozzle 102 thereto as shown in FIG. 1A which depicts a use-orientation of douche apparatus 100 (or 100*a* where nozzle 102*a* is substituted for nozzle 102). Namely, O-ring 215 may be seated in bottle adapter 114 as indicated by arrow 225, O-ring 217 may be seated in bottle adapter 116 as indicated by arrow 227, and O-ring 219 may be seated in bottle adapter 118 as indicated by arrow 229. O-ring 215 may provide a liquid seal between bottle adapter 114 and bottle adapter 116. O-ring 217 may provide a liquid seal between bottle adapter 116 and bottle adapter 118. O-ring 219 may provide a liquid seal between bottle adapter 118 and a liquid container comprising a threaded opening having male threads of a third type such as bottle 230*a* discussed above in conjunction with FIG. 2A. O-ring 302 may provide a liquid seal between nozzle 102 (or (102*a*) and bottle adapter 114 when seated in bottle adapter 114 (as indicated by arrow 322) and nozzle attachment feature 103 of nozzle 102 (or 102*a*) is mated with nozzle attachment end 142 comprising a mating feature mateable to nozzle attachment feature 103, such as threads 304 of bottle adapter 114 at a nozzle attachment end 142 of adapter assembly 120 (and bottle adapter 114 which forms portions of adapter assembly 120) opposite bottle attachment end 144, and seated against O-ring 302 in the orientation shown in FIG. 1A (and FIG. 1D). As will be apparent to those skilled in the art, in some implementations mating features other than threads depicted in nozzle attachment feature 103 and threads 304 are possible and within the scope of the appended claims, such as a bayonet mount or other such suitable mateable features. In some implementations, sealing members of other types than those of O-ring 302, O-ring 215, O-ring 217 and O-ring 219 may be used, such as rubber washers, gaskets and the like. In some implementations, nozzle attachment feature 103 and a mating feature of nozzle attachment end 142 may be a ½ inch male NPS (National Pipe Straight of the American National Standard Pipe Thread standard) thread and ½ inch female NPS thread, respectively, where NPS refers to s; or in some implementations nozzle attachment feature 103 and a mating feature of nozzle attachment end 142 may be a ½ inch male BSP (British Standard Pipe standards) parallel thread and ½ inch female BSP parallel thread, respectively, or some other suitable thread.

Bottle adapter 114, bottle adapter 116 and bottle adapter 118 may comprise nubs Bottle adapter 114, bottle adapter 116 and bottle adapter 118 may comprise a plurality of nubs, such as nub 324, nub 326 and nub 328, respectively, which may facilitate a grip when assembling, disassembling, using and handling douche apparatus 100 (or 100*a* or 101). As will be apparent to those skilled in the art, many various forms of surface configurations may be implemented which may facilitate a grip, such as ridges, dimples, textures and the like. Preferably the surface configuration may be readily cleanable facilitating a user's thorough cleansing of the apparatus following use to minimize residual douching material, bacteria and the like.

FIG. 3A may be instructive in discussing a storage-configuration of douche apparatus 101, as is shown in FIG. 1E. Douche apparatus 100 (or 100*a*) is depicted in a use-configuration in FIG. 1A (and FIG. 1D), and the orientation of nozzle 102 (or 102*a*) is changed to a storage-configuration shown in FIG. 1E and referenced as douche apparatus 101. To assemble douche apparatus in a storage-configuration of FIG. 1E, tip 106 (or 106*a*) is inserted into a central portion of adapter assembly 120 and nozzle attachment feature 103 may be mated with a mateable feature of bottle adapter 114 (e.g., threads 304) such that nozzle 102 (or 102*a*) may be situated wholly in a central portion of adapter assembly 120 as depicted in FIG. 1E, or in some implementations, a portion of nozzle 102 (or 102*a*) beyond nozzle attachment feature 103 may be situated in a central portion of adapter assembly 120, such as may be the case where in some implementations, nozzle 102 (or 102*a*) may be longer than adapter assembly 120 and a portion of nozzle 102 (or 102*a*0 necessarily extends beyond the length of adapter assembly 120.

As noted above, bottle adapter 118 may be configured for use with a liquid container comprising a threaded opening having male threads of a third type such as bottle 230*a* discussed above in conjunction with FIG. 2A. A use-configuration of douche apparatus 100 (or 100*a*) comprises adapter assembly 120 as depicted in FIG. 1A (or FIG. 1D), FIG. 2A and FIG. 3A. When attaching douche apparatus 100 (or 100*a*) to a liquid container comprising a threaded opening having male threads of a second type such as bottle 230*b* discussed above in conjunction with FIG. 2B, bottle adapter 118 is removed (along with O-ring 219 which may be seated therein) or are not present and bottle adapter 114 and bottle adapter 116 are configured (along with O-ring 302, O-ring 215 and O-ring 217 seated therein). When attaching douche apparatus 100 (or 100*a*) to a liquid container comprising a threaded opening having male threads of a first type such as bottle 230*c* discussed above in conjunction with FIG. 2C, bottle adapter 118 and bottle adapter 116 are removed (along with O-ring 219 and O-ring 217 which may be seated respectively therein) or are not present and bottle adapter 114 is configured (along with O-ring 302 and O-ring 215 seated therein).

FIG. 3B through FIG. 3G depict side elevation views and cross-sectional views of bottle adapter 114, bottle adapter 116 and bottle adapter 118 of the douche apparatus of FIG. 3A. FIG. 3B depicts a side elevation view of an example first bottle adapter 114 and indicates a section line 3C-3C. FIG. 3C depicts the indicated cross-section, wherein an attachment feature comprising female threads 304 (of a thread type configured to receive nozzle attachment feature 103 of nozzle 102) and female threads 334 of a first type are visible within the interior of bottle adapter 114. Also visible in FIG. 3C are an interior portion which may be called an “adapter central portion” though which a liquid may flow, and O-ring 302 and O-ring 215 seated within the interior of bottle adapter 114. FIG. 3D depicts a side elevation view of an example second bottle adapter 116, wherein male threads 306 of a first type are comprised by an adapter attachment end of bottle adapter 116 and are configured to mate with female threads 334 of a first type of bottle adapter 114. FIG. 3D indicates a section line 3E-3E. FIG. 3E depicts the indicated cross-section, wherein female threads 336 of a second type are visible within the interior of bottle adapter 116. Also visible in FIG. 3E are an interior portion which may be called an “adapter central portion” though which a liquid may flow, and O-ring 217 seated within the interior of bottle adapter 116. FIG. 3F depicts a side elevation view of an example third bottle adapter 118, wherein male threads 308 of a second type are comprised by an adapter attachment end of bottle adapter 118 and are configured to mate with female threads 336 of a second type of bottle adapter 116. FIG. 3F indicates a section line 3G-3G. FIG. 3G depicts the indicated cross-section, wherein female threads 338 of a third type are visible within the interior of bottle adapter 116. Also visible in FIG. 3E are an interior portion which may be called an “adapter central portion” though which a liquid may flow, and O-ring 219 seated within the interior of bottle adapter 118. One or more bottle adapters assembled in an adapter assembly such as adapter assembly 120, such as bottle adapter 114, bottle adapter 116 and bottle adapter 118 form a central portion of adapter assembly 120 which is comprised of central portions of bottle adapter 114, bottle adapter 116 and bottle adapter 118, wherein a liquid may flow through a central portion of adapter assembly 120 during use, and when not in use, a nozzle body, such as a portion of nozzle 102 extending from nozzle attachment feature 103 up to and including nozzle tip 106 (or 106*a*) of nozzle 102 (or 102*a*) may be situated wholly in a central portion of adapter assembly 120 as depicted in FIG. 1E, or in some implementations, a portion of nozzle 102 (or 102*a*) beyond nozzle attachment feature may be situated in a central portion of adapter assembly 120, such as may be the case where in some implementations, nozzle 102 (or 102*a*) may be longer than adapter assembly 120 and a portion of nozzle 102 (or 102*a*) extends beyond the length of adapter assembly 120.

Figures 4A, 4B, 4C, 4D, 4E:
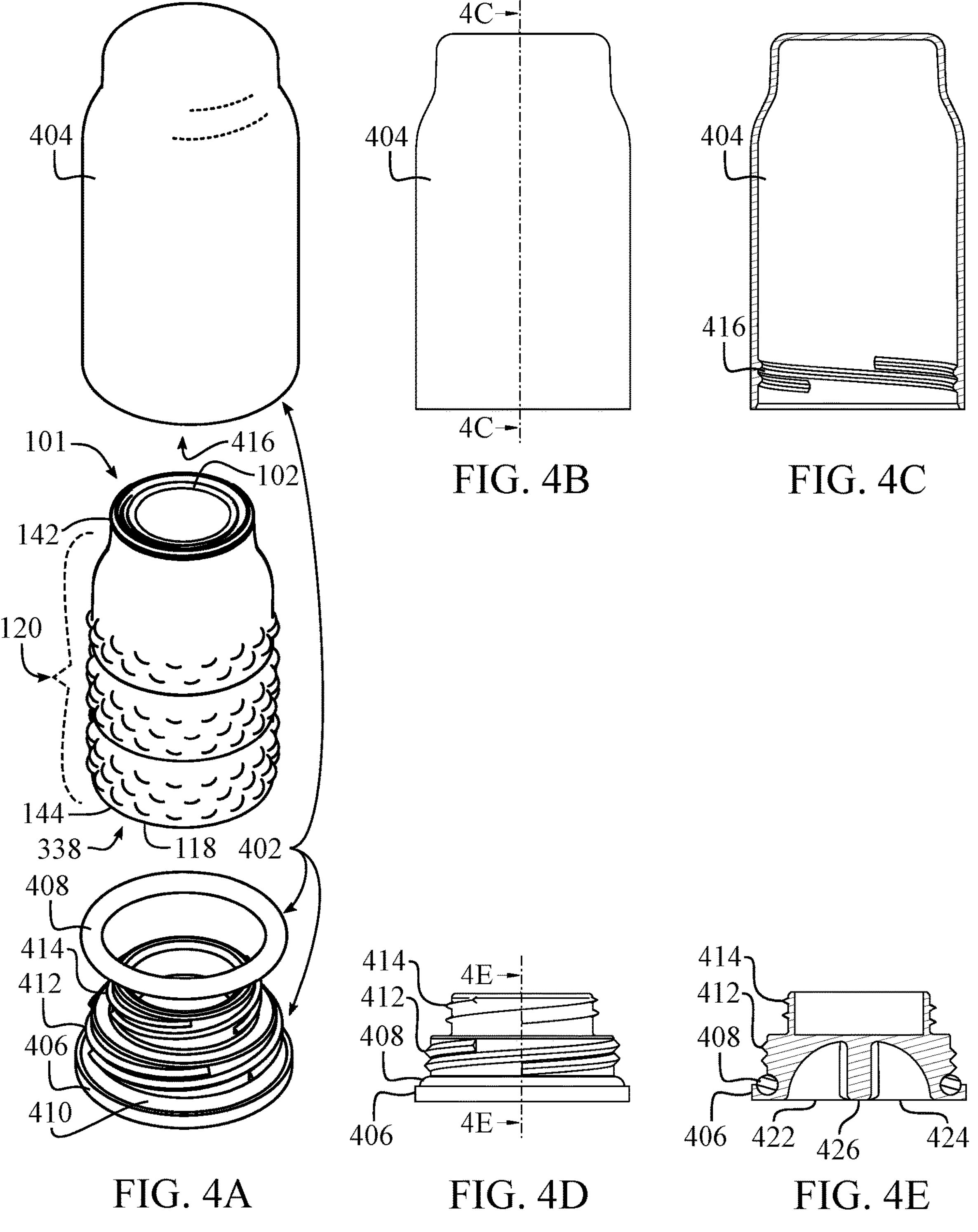
FIG. 4A depicts a perspective view of the example douche apparatus of FIG. 1A (or FIG. 1D) in a storage-orientation situated between components of an example storage case.
FIG. 4B depicts a side elevation view of a case housing of FIG. 4A.
FIG. 4C a cross-section of the case housing of FIG. 4B.
FIG. 4D depicts a side elevation view of a case cap of FIG. 4A.
FIG. 4E depicts a cross-section of the case cap of FIG. 4D.

FIG. 4A depicts a perspective view of an example douche apparatus 101 in storage-orientation, such as that disclosed in conjunction with FIG. 1E (and which may be douche apparatus 100 of FIG. 1A reconfigured from a use-orientation to a storage-orientation), situated between components of a storage case 402 comprising a case housing 404, a case cap 406 and an O-ring 408, wherein storage case 402 is useable to store and transport douche apparatus 101. Case cap 406 comprises an interior side (visible in FIG. 4A) which is directed towards an interior of case housing 404 (not visible in FIG. 4A) when removably attached thereto and an exterior side (not visible in FIG. 4A) which is directed away from case housing 404 when removably attached thereto. To store douche apparatus 101, O-ring 408 may be seated in O-ring seat 410 of cap 406, female threads 338 (see FIG. 3G) of bottle adapter 118 comprised by adapter assembly 120 may be threaded onto male threads 414 of cap 406 thereby removably attaching bottle attachment end 144 (opposite from nozzle attachment end 142) of adapter assembly 120 of douche apparatus 101 to case cap 406, and male threads 412 of cap 406 may be threaded into female threads 416 (see FIG. 4C) of case housing 404, wherein O-ring 408 may provide a liquid seal between case cap 406 and case housing 404 such that douche apparatus 101 may be safely stored and remain clean within case 402 until required, despite being carried in a portable fashion, such as in a pants-pocket, bag, purse, backpack and the like. Following use, douche apparatus 101 may be returned to a storage-orientation and may be safely stored until a user may clean douche apparatus 101 and case 402 and store douche apparatus 101 within case 402 such that it is prepared for future use. Due to an attachment of douche apparatus 101 to case cap 406 and an attachment of case cap 406 to case housing 404, a rattling of douche apparatus 101 within case 402 may be prevented.

FIG. 4B depicts a side elevation view of case housing 404 of FIG. 4A and indicates a section line 4C-4C. FIG. 4C depicts the indicated cross-section, wherein female threads 416 of case housing 404 are configured to receive male threads 412 of case cap 406. FIG. 4D depicts a side elevation view of case cap 406 of FIG. 4A and indicates a section line 4E-4E. FIG. 4E depicts the indicated cross-section, wherein male threads 414 are configured to receive female threads 338 of bottle adapter 118 comprised by adapter assembly 120 and male threads 412 are configured to receive female threads 416 of case housing 404. Case cap 406 comprises a recess area 422 and a recess area 424 proximate to a graspable member 426, wherein a user may insert a thumb and finger into recess area 422 and recess area 424 and grasp case cap 406 by graspable member 426 to facilitate assembly and disassembly of douche apparatus 101 to case cap 406 and case cap 406 to case housing 404. In some implementations, recess area 422 and recess area 424 may be two recesses fully separated by graspable member 426; in some implementations, recess area 422 and recess area 424 may be two areas of a single recess having graspable member 526 situated therein (such as a raised three sided tab), or some other suitable configuration of one or more recesses and at least one graspable member.

Figures 5A, 5B, 5C, 5D, 5E, 5F:
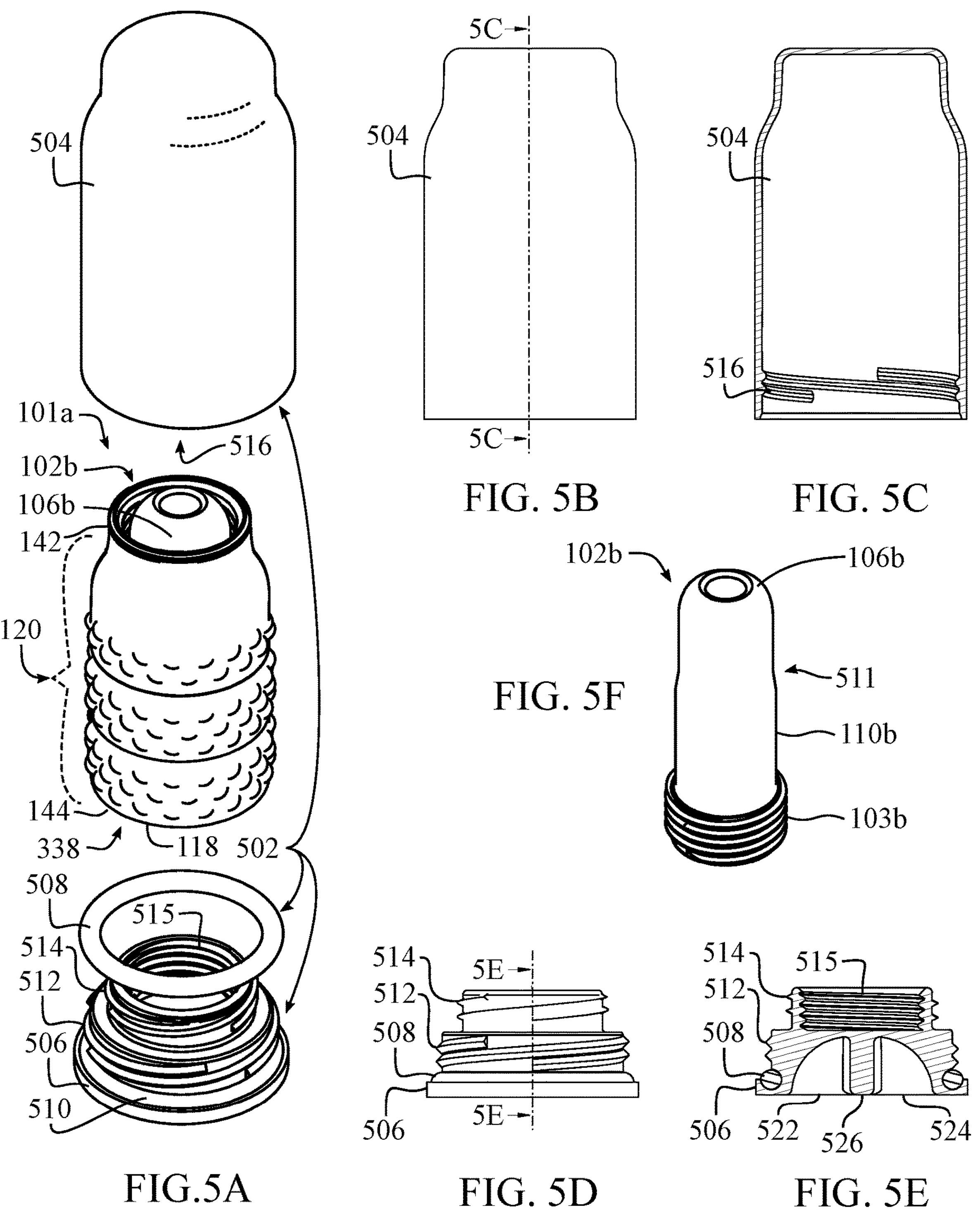
FIG. 5A depicts a perspective view of an example douche apparatus of the present invention in a storage-orientation situated between components of an example storage case.
FIG. 5B depicts a side elevation view of a case housing of FIG. 5A.
FIG. 5C a cross-section of the case housing of FIG. 5B.
FIG. 5D depicts a side elevation view of a case cap of FIG. 5A.
FIG. 5E depicts a cross-section of the case cap of FIG. 5D.
FIG. 5F depicts a perspective view of an example implementation of a nozzle.

In some implementations, a douche apparatus may be configured such that a storage-orientation comprises a nozzle situated in a central portion of an adapter assembly with the nozzle nozzle tip directed outward from the nozzle attachment end. FIG. 5A depicts a perspective view of an example douche apparatus 101*a* in a storage-orientation comprising a nozzle 102*b* situated having nozzle tip 106*b* directed outward from nozzle attachment end 142 and a nozzle body which may be a portion of nozzle 102*b* extending from nozzle attachment feature 103*b* (see FIG. 5F) up to and including nozzle tip 106*b*, and the nozzle body may be wholly situated in a central portion of adapter assembly 120 as depicted in FIG. 5A, or in some implementations, a portion of nozzle 102*b* beyond a nozzle attachment feature may be situated in a central portion of adapter assembly 120, such as may be the case where in some implementations, nozzle 102*b* may be longer than adapter assembly 120 and a portion of nozzle 102*b* extends beyond the length of adapter assembly 120. In some implementations, nozzle 102*b* of douche apparatus 101*a* may be attached to case cap 506 which may in turn be attached to adapter assembly 120. Douche apparatus 101*b* may be situated between components of a storage case 502 comprising a case housing 504, a case cap 506 and an O-ring 508, wherein storage case 502 may be useable to store and transport douche apparatus 101*a*. To store douche apparatus 101*a*, nozzle attachment feature 103*b* (see FIG. 5F) of nozzle 102*b* may be mated to a corresponding attachment feature of case cap 506, such as female threads 515 of case cap 506, O-ring 508 may be seated in O-ring seat 510 of cap 506, and female threads 338 (see FIG. 3G) of bottle adapter 118 comprised by bottle attachment end 144 of adapter assembly 120 may be threaded onto male threads 514 of case cap 506 thereby removably attaching bottle attachment end 144 (opposite from nozzle attachment end 142) of adapter assembly 120 of douche apparatus 101*a* to case cap 506, and male threads 512 of cap 506 may be threaded into female threads (not visible in FIG. 5A) of case housing 504, wherein O-ring 508 may provide a liquid seal between case cap 506 and case housing 504 such that douche apparatus 101*a* may be safely stored and remain clean within case 502 until required, despite being carried in a portable fashion, such as in a pants-pocket, bag, purse, backpack and the like. Following use, douche apparatus 101*a* may be returned to a storage-orientation and may be safely stored until a user may clean douche apparatus 101*a* and case 502 and store douche apparatus 101*a* within case 502 such that it is prepared for future use. Due to an attachment of douche apparatus 101*a* to case cap 506 and an attachment of case cap 506 to case housing 504, a rattling of douche apparatus 101*a* within case 502 may be prevented.

FIG. 5B depicts a side elevation view of case housing 504 of FIG. 5A and indicates a section line 5C-5C. FIG. 5C depicts the indicated cross-section, wherein female threads 516 are configured to receive male threads 512 of case cap 506. FIG. 5D depicts a side elevation view of case cap 506 of FIG. 5A and indicates a section line 5E-5E. FIG. 5E depicts the indicated cross-section, wherein an attachment feature, such as female threads 515 are configured to receive nozzle attachment feature 103*b* of nozzle 102*b* (see FIG. 5F), male threads 514 are configured to receive female threads 338 of bottle adapter 118 comprised by adapter assembly 120 and male threads 512 are configured to receive female threads 516 of case housing 504. Case cap 506 comprises a recess area 522 and a recess area 524 proximate to a graspable member 526, wherein a user may insert a thumb and finger into the recess area 522 and recess area 524 and grasp case cap 506 by graspable member 526 to facilitate assembly and disassembly of douche apparatus 101*a* to case cap 506 (wherein nozzle 102*b* and adapter assembly 120 are each removably attachable to case cap 506) and case cap 506 to case housing 504. In some implementations, recess area 522 and recess area 524 may be formed by two separate recesses, each comprising a recess area fully separated by graspable member 526; in some implementations, recess area 522 and recess area 524 may be two recess areas of a single recess having graspable member situated therein (such as a raised three sided tab), or some other suitable configuration of one or more recesses and at least one graspable member.

FIG. 5F depicts a perspective view of an example implementation of nozzle 102*b* comprising a nozzle wall 110*b*, wherein nozzle wall 110*b* may have a taper 511 to a smaller diameter such that the upper portion of nozzle 102*b* may pass within/through O-ring 302 of bottle adapter 114 (see FIG. 3C). In some implementations, wall 110*b* may be of a uniform diameter configured to pass within/through O-ring 302. A nozzle body may be a portion of nozzle 102*b* extending from nozzle attachment feature 103*b* up to and including nozzle tip 106*b*.

Figures 6A, 6B, 6C, 6D, 6E, 6F:
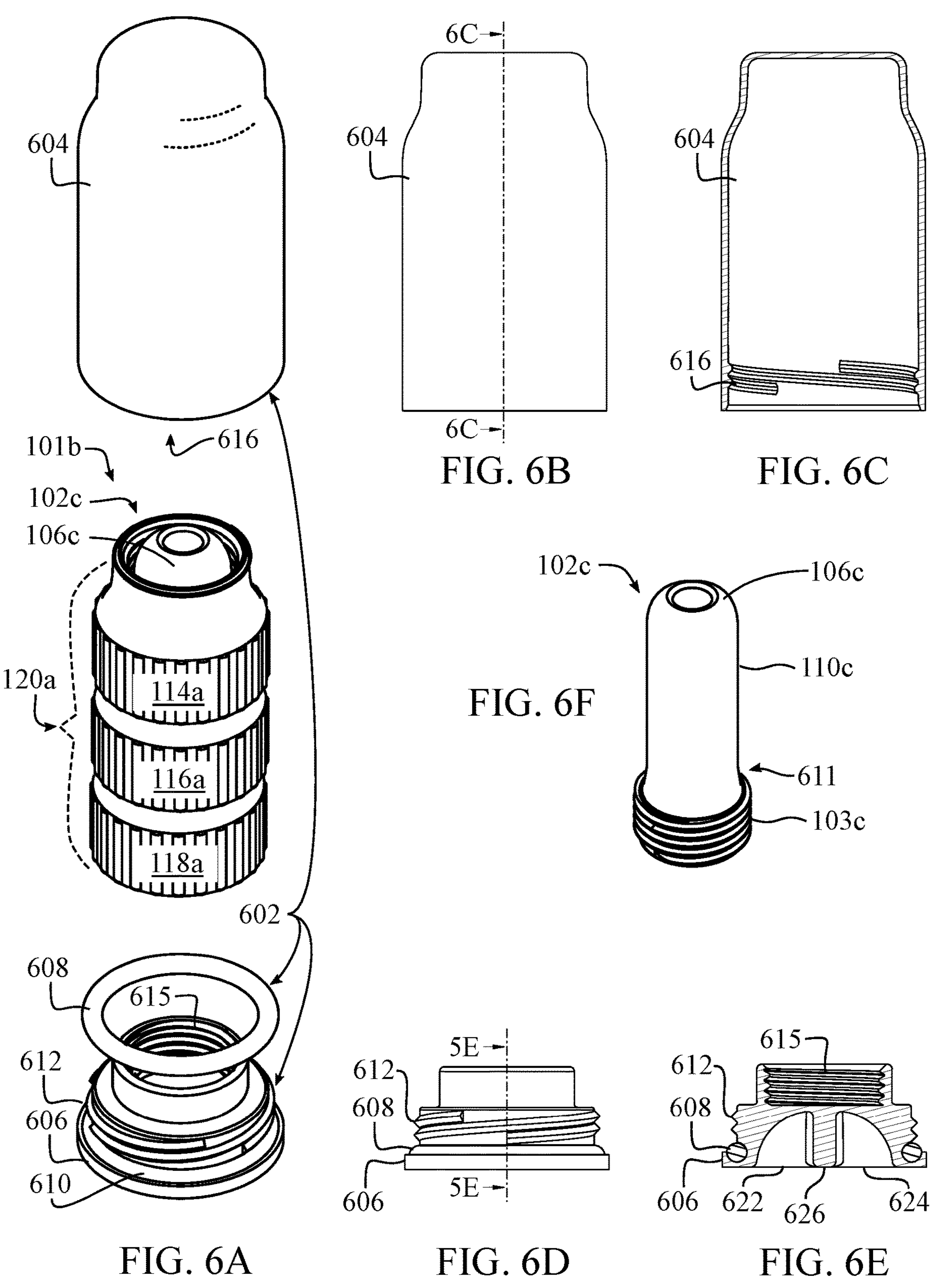
FIG. 6A depicts a perspective view of an example douche apparatus of the present invention in a storage-orientation situated between components of an example storage case.
FIG. 6B depicts a side elevation view of a case housing of FIG. 6A.
FIG. 6C a cross-section of the case housing of FIG. 6B.
FIG. 6D depicts a side elevation view of a case cap of FIG. 6A.
FIG. 6E depicts a cross-section of the case cap of FIG. 6D.
FIG. 6F depicts a perspective view of an example implementation of a nozzle.

In some implementations, a douche apparatus may comprise one or more bottle adapters which do not mate with each other (e.g., do not interlock) as do bottle adapter 114, bottle adapter 116 and bottle adapter 118 in adapter assembly 120 disclosed in conjunction with FIGS. 3A-3G. FIG. 6A depicts a perspective view of an example douche apparatus 101*b* of the present invention comprising three bottle adapters, wherein FIG. 6A depicts douche apparatus 101*b* in a storage-orientation comprising a nozzle 102*c* situated having nozzle tip 106*c* directed outward from adapter assembly 120*a* and a nozzle body which may be a portion of nozzle 102*c* extending from nozzle attachment feature 103*c* (see FIG. 6F) up to and including nozzle tip 106*c*, and the nozzle body may be wholly situated in a central portion of adapter assembly 120*a* as depicted in FIG. 6A, or in some implementations, a portion of nozzle 102*c* beyond a nozzle attachment feature 103*c* may be situated in a central portion of adapter assembly 120, such as may be the case where in some implementations, nozzle 102*c* may be longer than adapter assembly 120 and a portion of nozzle 102*c* extends beyond the length of adapter assembly 120. Douche apparatus 101*b* is depicted in a storage-orientation comprising a nozzle 102*c* situated in a central portion of an adapter assembly 120*a* having nozzle tip 106*c* directed upward. Bottle adapter 114*a*, bottle adapter 116*a* and bottle adapter 118*a* may be arranged in a stack and may not be secured together. Douche apparatus 101*b* may be situated between components of a storage case 602 comprising a case housing 604, a case cap 606 and an O-ring 608, wherein storage case 602 is useable to store and transport douche apparatus 101*b*. To store douche apparatus 101*b*, a nozzle attachment feature 103*c* (see FIG. 6F) of nozzle 102*c* may mated with an attachment feature of case cap 606, such as female threads 615, bottle adapter 118*a*, bottle adapter 116*a* and bottle adapter 114*a* may be stacked on case cap 606 with nozzle 102*c* passing through central portions thereof, O-ring 608 may be seated in O-ring seat 610 of cap 606, and male threads 612 of cap 606 may be threaded into female threads 616 (see FIG. 6C) of case housing 604, wherein O-ring 608 may provide a liquid seal between case cap 606 and case housing 604 such that douche apparatus 101*b* may be safely stored and remain clean within case 602 until required, despite being carried in a portable fashion, such as in a pants-pocket, bag, purse, backpack and the like. Following use douche apparatus 101*b* may be returned to a storage-orientation and may be safely stored until a user may clean douche apparatus 101*b* and case 602 and store douche apparatus 101*b* within case 602 such that it may be prepared for future use.

FIG. 6B depicts a side elevation view of case housing 604 of FIG. 6A and indicates a section line 6C-6C. FIG. 6C depicts the indicated cross-section, wherein female threads 616 are configured to receive male threads 612 of case cap 606. FIG. 6D depicts a side elevation view of case cap 606 of FIG. 6A and indicates a section line 6E-6E. FIG. 6E depicts the indicated cross-section, wherein an attachment feature, such as female threads 615 are configured to receive nozzle attachment feature 103*c* of nozzle 102*c* (see FIG. 6F) and male threads 612 are configured to receive female threads 616 of case housing 604. Case cap 606 comprises a recess area 622 and a recess area 624 proximate to a graspable member 626, wherein a user may insert a thumb and finger into the recess area 622 and recess area 624 and grasp case cap 606 by a graspable member 626 to facilitate assembly and disassembly of douche apparatus 101*b* to case cap 606 and case cap 606 to case housing 604. In some implementations, recess area 624 and recess area 624 may be two recesses fully separated by graspable member 626; in some implementations, recess area 622 and recess area 624 may be two areas of a single recess having graspable member 626 situated therein (such as a raised three sided tab), or some other suitable configuration of one or more recesses and at least one graspable member FIG. 6F depicts a perspective view of an example implementation of nozzle 102*c* comprising a nozzle attachment feature 103*c* configured to mate with an attachment feature, such as threads 615 of case cap 606, and a nozzle wall 110*c*, wherein nozzle wall 110*c* may have a taper 611 to a smaller diameter such that an upper portion of nozzle 102*c* may pass within/through bottle adapter 114*a*, bottle adapter 116*a* and bottle adapter 118*a*. In some implementations, wall 110*c* may be of a uniform diameter configured to pass within/through bottle adapter 114*a*, bottle adapter 116*a* and bottle adapter 118*a*.

FIG. 7A through FIG. 7F depict side elevation views and cross-sectional views of bottle adapter 114*a*, bottle adapter 116*a* and bottle adapter 118*a*. FIG. 7A depicts a side elevation view of a first bottle adapter 114*a* of the douche apparatus of FIG. 6A and indicates a section line 7B-7B. FIG. 7B depicts the indicated cross-section, wherein an attachment feature, such as female threads 704 are configured to nozzle attachment feature 103*c* of nozzle 102*c* (see FIG. 6F) and female threads 734 of a first type compatible with a bottle comprising male threads of a first type (such as threads 232*c* of FIG. 2C) are visible within the interior of bottle adapter 114*a*. Also visible in FIG. 7B are nozzle O-ring 702 and bottle O-ring 715 seated within the interior of bottle adapter 114*a*. FIG. 7C depicts a side elevation view of a second bottle adapter 116*a* of the douche apparatus of FIG. 6A and indicates a section line 7D-7D. FIG. 7D depicts the indicated cross-section, wherein an attachment feature, such as female threads 704 configured to mate with nozzle attachment feature 103*c* of nozzle 102*c* (see FIG. 6F) and female threads 736 of a second type compatible with a bottle comprising male threads of a second type (such as threads 232*b* of FIG. 2B) are visible within the interior of bottle adapter 116*a*. Also visible in FIG. 7D are nozzle O-ring 702 and bottle O-ring 717 seated within the interior of bottle adapter 116*a*. FIG. 7E depicts a side elevation view of a third bottle adapter 118*a* of the douche apparatus of FIG. 6A and indicates a section line 7F-7F. FIG. 7F depicts the indicated cross-section, wherein an attachment feature, such as female threads 704 configured to mate with nozzle attachment feature 103*c* of nozzle 102*c* (see FIG. 6F) and female threads 738 of a third type compatible with a bottle comprising male threads of a third type (such as threads 232*a* of FIG. 2A) are visible within the interior of bottle adapter 118*a*. Also visible in FIG. 7F are nozzle O-ring 702 and bottle O-ring 719 seated within the interior of bottle adapter 118*a*.

Figure 7G:
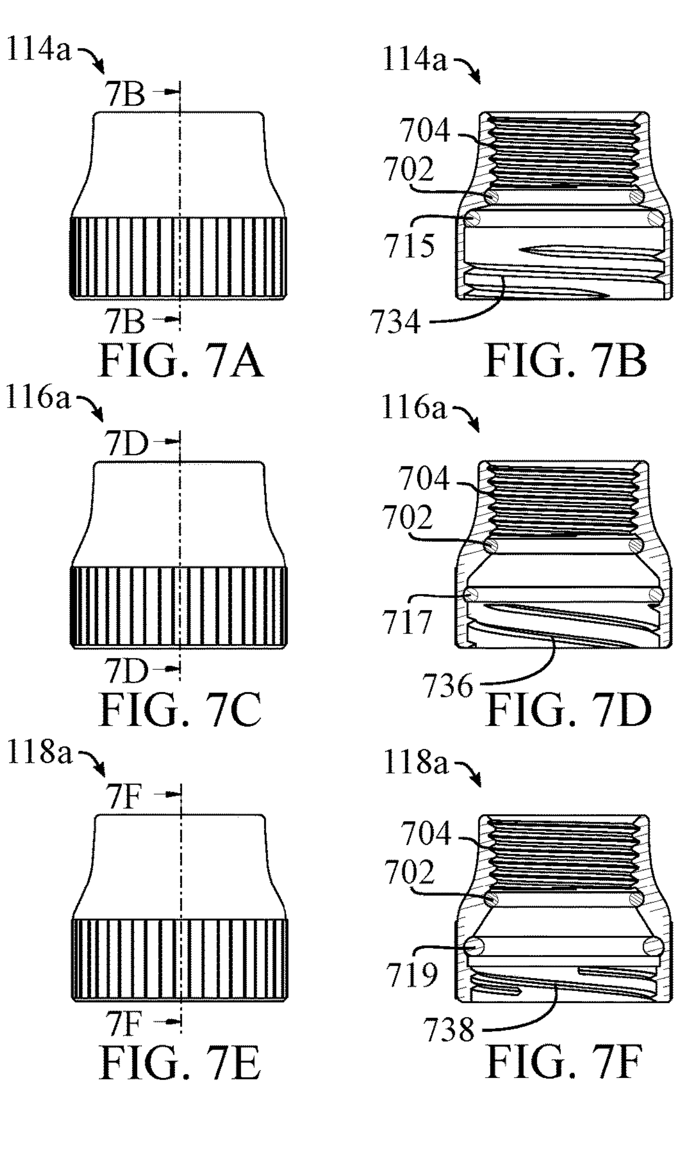
FIG. 7G depicts a partial perspective view of a squeezable bottle having attached the douche apparatus of FIG. 6A.
Figure 7G:
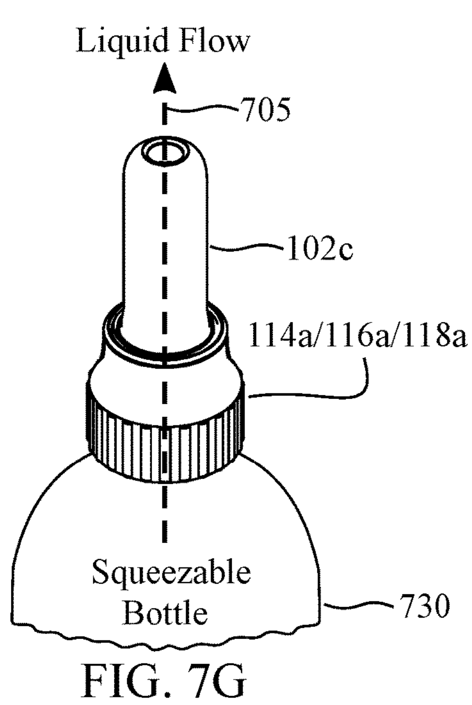

FIG. 7G depicts a partial perspective view of a squeezable bottle 730, such as a conventional plastic water bottle, having an attached douche apparatus of FIG. 6A, such as douche apparatus 101*b* configured for use and comprising a bottle adapter which may be one of 114*a*, 116*a* and 118*a* and may be representative of a bottle comprising a thread of one of a first type, a second type and a third type, respectively, such as bottles depicted in FIG. 2C, FIG. 2B and FIG. 2A, respectively, having threads 232*c*, threads 232*b* and threads 232*a*, respectively. When assembled as shown in FIG. 7G, nozzle O-ring 702 and bottle O-ring 715, nozzle O-ring 702 and bottle O-ring 717, or nozzle O-ring 702 and bottle O-ring 719 of bottle adapter 114*a*, bottle adapter 116*a* or bottle adapter 118*a*, respectively, may provide liquid seals between a bottle, such as example squeezable bottle 730 having threads of a first type, second type or third type, respectively, and when filled with a liquid and squeezed, liquid may flow from squeezable bottle 730 through a central portion of bottle adapter 114*a*, bottle adapter 116*a* or bottle adapter 118*a*, respectively, and through a channel of nozzle 102*c* and be dispensed from an orifice of nozzle 102*c* as indicated by arrow 705 indicating a path and flow of liquid.

Figures 8A, 8B, 8C, 8D, 8F:
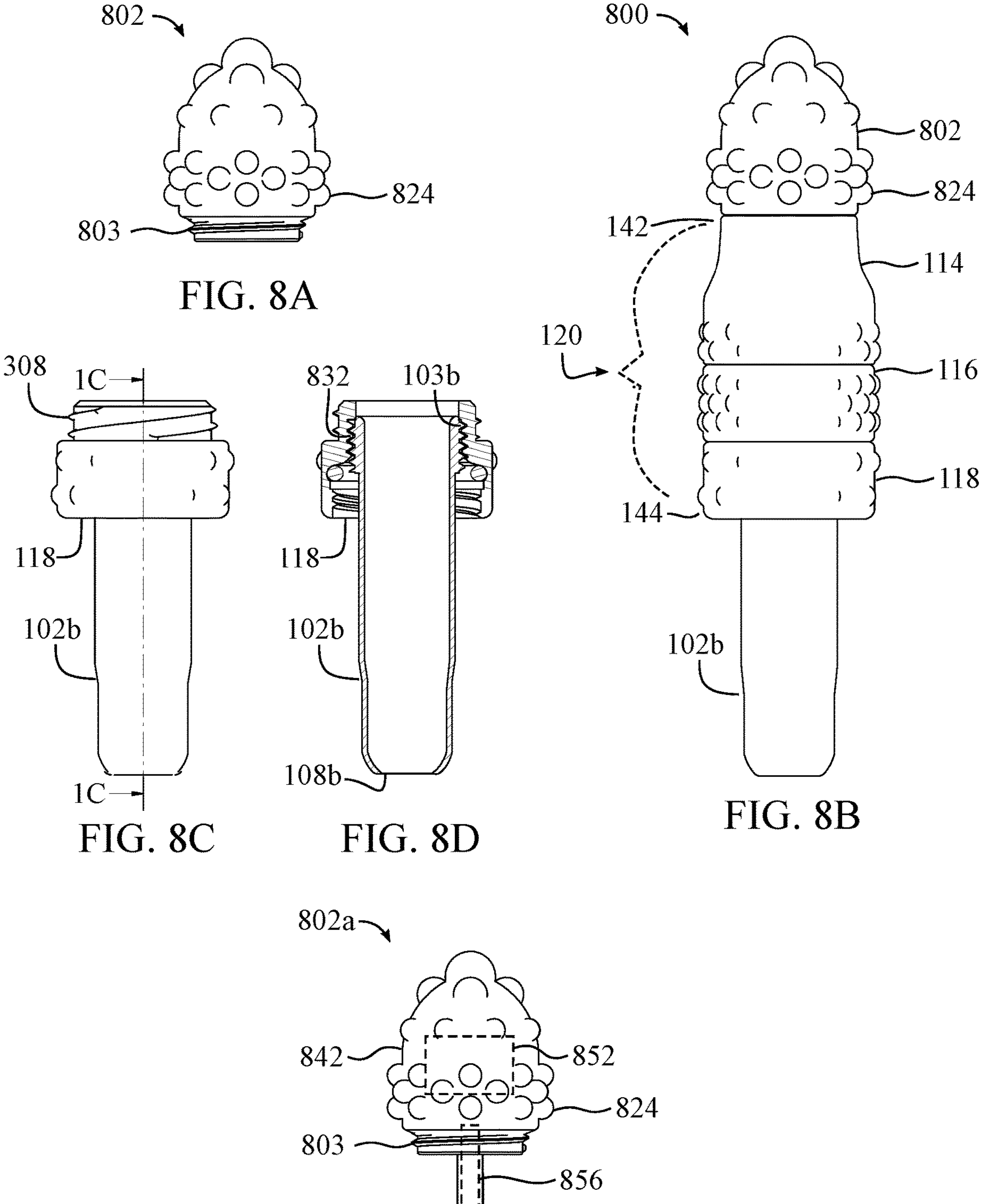
FIG. 8A depicts a side elevation view of an example stimulation device.
FIG. 8B depicts a side elevation view of an example douche apparatus of the present invention further comprising a stimulation device.
FIG. 8C depicts a side elevation view of a nozzle attachable as a handle for the douche apparatus of FIG. 8B comprising a stimulation device.
FIG. 8D depicts a cross-section of the nozzle attachable as a handle of FIG. 8C.
FIG. 8F depicts a stimulation device having a vibrator mechanism.

In some implementations, a douche apparatus, such as douche apparatus 100 (or 100*a*) may further comprise stimulation device which may be removably attached to an adapter assembly, such as adapter assembly 120 of FIG. 3A, as a sexual stimulation apparatus. FIG. 8A depicts a side elevation view of an example stimulation device 802 comprising a plurality of nubs, such as nub 824 and a device attachment feature 803 which may be configured to mate with nozzle attachment end 142 of adapter assembly 120 (FIG. 3A). FIG. 8B depicts a side elevation view of an example douche apparatus 800 of the present invention further comprising a stimulation device 802, wherein stimulation device 802 is attached to adapter assembly 120 at nozzle attachment end 142. In some implementations, bottle adapter 118 may be configured to removably attach to a nozzle, such as nozzle 102*b* (see FIG. 5F) which may serve as a handle for douche apparatus 800, wherein FIG. 8C and FIG. 8D depict a side elevation of bottle adapter 118 and nozzle 102*b* indicating a section line and a side elevation of the indicated cross-section, respectively, and such cross-section of FIG. 8D shows an attachment feature, such as threads 832 mateable to a nozzle attachment feature 103*b*. In some implementations, an elongated storage case such as a longer implementation of storage case 502 (see FIG. 5A) which may be increased in length by an amount sufficient to allow storage of stimulation apparatus 800 and a nozzle, such as nozzle 102*b* (FIG. 5A) situated within a central portion of adapter assembly 120, wherein both nozzle 102*b* and adapter assembly 120 (comprising stimulation device 802) may be attached to case cap 506 as disclosed in conjunction with FIG. 5A.

In some implementations, a stimulation cap may be an electromechanical device comprising a vibrator mechanism and a power source for powering the vibrator mechanism. FIG. 8F depicts a stimulation device 802*a* having a plurality of nubs on an upper portion 842, such as nub 824, a vibrator mechanism 852, a battery housing 854 and a battery 856 within battery housing 854 configured to power vibrator mechanism 852. In some implementations, a rotation of battery housing 854 relative to upper portion 842 may cause completion of a circuit between battery 856 and vibrator mechanism 852, such that battery housing 854 may function as a switch usable to turn on and turn off vibrator mechanism 852. In some implementations, battery housing 854 may be configured to fit through an orifice 108*b* of nozzle 102*b* and be situated at least partially within a nozzle body of nozzle 102*b* when stimulation apparatus 800 is assembled in a storage-configuration.

A number of implementations of a douche apparatus have been disclosed. Various modifications may be made without departing from the spirit and scope of the disclosed douche apparatus and the appended claims. In some implementations, components of douche apparatus disclosed herein may be constructed of a medical grade plastic or some other plastic suitable for intimate bodily contact. In some implementations, such components may be produced using thermoplastic injection molding processes and/or thermoforming processes. In some implementations, other processes may be used such as 3D printing. In some implementations, components of douche apparatus disclosed herein may be constructed of metals, such as stainless steel. In some implementations, such components may be produced using metal forming processes and/or metal machining processes. In some implementations, a combination of metal components and plastic components may employed. In some implementations, O-rings, rubber washers and gaskets may be sourced from commonly available parts. In some implementations, a nozzle may further comprise a check valve configured to allow liquid to flow through a nozzle channel and dispense through a nozzle orifice but check (prevent) a liquid flow in a reverse direction thereof.

The present disclosure is not to be limited in terms of the particular implementations described in this application, which are intended as example implementations of various aspects. Moreover, the various disclosed implementations can be interchangeably used with each other, unless otherwise noted. Many modifications and variations can be made without departing from the spirit and scope of the present disclosure and appended claims, as will be apparent to those skilled in the art. Functionally equivalent methods, components and apparatuses within the scope of the disclosure, in addition to those enumerated herein will be apparent to those skilled in the art from the foregoing descriptions. Such modifications and variations are intended to fall within the scope of the appended claims. It is also to be understood that the terminology used herein is for the purpose of describing particular implementations only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

A number of implementations of the douche apparatus have been described. Various modifications may be made without departing from the spirit and scope of the invention.

What is claimed is:

1. A douche apparatus comprising:

a nozzle having a nozzle channel, a proximate end having a nozzle attachment feature, a distal end having a nozzle tip and a nozzle body extending from the nozzle attachment feature up to and including the nozzle tip comprising a nozzle wall circumscribing the nozzle channel, wherein the nozzle has at least one orifice disposed on the nozzle tip or the nozzle wall;

a bottle adapter assembly having two or more interconnectable bottle adapters, wherein:

a first bottle adapter comprises a first bottle attachment end having first bottle attachment threads compatible with bottles having a first thread type, a nozzle attachment end configured to removably attach to the nozzle attachment feature and a first bottle adapter central portion situated between the first bottle attachment end and the nozzle attachment end; and a second bottle adapter comprises a second bottle attachment end having second bottle attachment threads compatible with bottles having a second thread type, a first bottle adapter attachment end having threads configured to removably attach to the first bottle attachment end and a second bottle adapter central portion situated between the second bottle attachment end and the first bottle adapter attachment end, wherein:

the douche apparatus is configurable for use with bottles having threads of the first type and bottles having threads of the second type, wherein:

when configured for use with a bottle having the first thread type, the nozzle attachment feature is attached to the nozzle attachment end with the nozzle body directed away from the first bottle adapter and the first bottle attachment end is attachable to the bottle having the first thread type from which a liquid may flow through the first bottle adapter central portion, through the nozzle channel and out of the at least one orifice; and when configured for use with a bottle having the second thread type, the nozzle attachment feature is attached to the nozzle attachment end with the nozzle body directed away from the first bottle adapter, the first bottle attachment end is attached to the first bottle adapter attachment end of the second bottle adapter, thereby interconnecting the first bottle adapter and the second bottle adapter, and the second bottle attachment end is attachable to the bottle having the second thread type from which a liquid may flow through the second bottle adapter central portion, through the first bottle adapter central portion, through the nozzle channel and out of the at least one orifice; and the douche apparatus is configurable for storage and portability, wherein when configured for storage and portability, the two or more bottle adapters of the bottle adapter assembly are interconnected and the nozzle is situated to at least partially occupy central portions of at least two of the two or more interconnected bottle adapters.

2. The douche apparatus of claim 1, wherein the bottle adapter assembly further comprises a third bottle adapter comprising a third bottle attachment end having third bottle attachment threads compatible with bottles having a third thread type, a second bottle adapter attachment end having threads configured to interconnect to the second bottle attachment end and a third bottle adapter central portion situated between the third bottle attachment end and the second bottle adapter attachment end, wherein the douche apparatus is further configurable for use with a bottle having threads of the third type, wherein the nozzle attachment feature is attached to the nozzle attachment end with the nozzle body directed away from the first bottle adapter, the first bottle attachment end is attached to the first bottle adapter attachment end of the second bottle adapter, thereby interconnecting the first bottle adapter and the second bottle adapter, the second bottle attachment end is attached to the second bottle adapter attachment end of the third bottle adapter, thereby interconnecting the third bottle adapter to the interconnected first bottle adapter and the second bottle adapter, and the third bottle attachment end is attachable to the bottle having the third thread type from which a liquid may flow through the third bottle adapter central portion, through the second bottle adapter central portion, through the first bottle adapter central portion, through the nozzle channel and out of the at least one orifice.

3. The douche apparatus of claim 1, wherein when configured for storage and portability, the nozzle body may be longitudinally situated wholly within the central portions of the two or more interconnected bottle adapters of the bottle adapter assembly.

4. The douche apparatus of claim 1, wherein when configured for storage and portability, the nozzle attachment feature is removably attached to the nozzle attachment end.

5. The douche apparatus of claim 1, further comprising a case having a case housing and a case cap, wherein:

the bottle adapter assembly comprises interconnected bottle adapters comprising the first bottle adapter, wherein the nozzle attachment feature is disposed on a first end of the bottle adapter assembly and a second end of the bottle adapter assembly distal from the first end comprises bottle attachment threads;

the case cap is removably attachable to the case housing;

the case cap has an exterior side and an interior side, wherein, when attached to the case housing, the interior side is directed towards an interior of the case housing and comprises threads mateable to the bottle attachment threads of the second end, wherein when the nozzle and bottle adapter assembly are stored within the case, the bottle adapter assembly and the case are removably attached to the interior side of the case cap, the case cap is removably attached to the case housing and the bottle adapter assembly is thereby secured to the case when stored therein.

6. The douche apparatus of claim 5, wherein the case cap further comprises threads mateable to the nozzle attachment feature, wherein the nozzle is configured to be removably attached to the interior side of the case cap and be situated at least partially within central portions of two of the two or more bottle adapters of the bottle adapter assembly.

7. The douche apparatus of claim 5, wherein the exterior side of the case cap comprises a recess area proximate to a graspable member of the case cap.

8. The douche apparatus of claim 1, further comprising a stimulation device removably attachable to the nozzle attachment end of the adapter assembly.

9. The douche apparatus of claim 8, wherein the stimulation device comprises a vibrator mechanism and a power source for the vibrator mechanism.

10. The douche apparatus of claim 1, further comprising a check valve, wherein the check valve is configured to allow liquid to flow through the nozzle channel and dispense through the at least one orifice and prevent liquid from flowing in a reverse direction thereof.

11. The douche apparatus of claim 1, wherein each of the one or more bottle adapters comprises a plurality of nubs configured to facilitate a grip thereon.

* * * * *